(12) United States Patent
Keller

(10) Patent No.: US 8,157,808 B2
(45) Date of Patent: Apr. 17, 2012

(54) INSERTION INSTRUMENT FOR AN ENDOPROSTHESIS COMPRISING A PROSTHESIS SHAFT WHICH IS TO BE INSERTED INTO A MEDULLARY CAVITY

(75) Inventor: Arnold Keller, Kayhude (DE)

(73) Assignee: Waldemar Link GmbH & Co. KG, Hamburg (DE)

( * ) Notice: Subject to any disclaimer, the term of this patent is extended or adjusted under 35 U.S.C. 154(b) by 742 days.

(21) Appl. No.: 11/997,593

(22) PCT Filed: Sep. 6, 2006

(86) PCT No.: PCT/EP2006/008679
§ 371 (c)(1),
(2), (4) Date: Feb. 1, 2008

(87) PCT Pub. No.: WO2007/028588
PCT Pub. Date: Mar. 15, 2007

(65) Prior Publication Data
US 2008/0221576 A1    Sep. 11, 2008

(30) Foreign Application Priority Data
Sep. 9, 2005 (DE) .......................... 20 2005 014 270

(51) Int. Cl.
*A61B 17/58* (2006.01)
*A61B 17/60* (2006.01)
*A61F 2/00* (2006.01)
(52) U.S. Cl. ........................................... 606/99; 606/89
(58) Field of Classification Search .................... 606/89, 606/99
See application file for complete search history.

(56) References Cited

U.S. PATENT DOCUMENTS
4,936,863 A    6/1990   Hofmann
6,110,179 A *  8/2000   Flivik et al. ...................... 606/99
(Continued)

FOREIGN PATENT DOCUMENTS
DE        21 01 002 B    5/1972
(Continued)

OTHER PUBLICATIONS
International Search Report from corresponding International Application No. PCT/EP2006/008679 dated May 15, 2007.

*Primary Examiner* — Thomas C. Barrett
*Assistant Examiner* — Christine Nelson
(74) *Attorney, Agent, or Firm* — Lempia Summerfield Katz LLC

(57) ABSTRACT

The invention relates to an insertion instrument for an endoprosthesis (1), which comprises a neck part (12) and a shaft part (10) which is to be inserted into a medullary cavity, comprising a clamping device (2) which is provided with a holding fork (25) and a thrust bearing (26), which are embodied in such a manner that the endoprosthesis (1) is held fixedly in a clamped state and is released in an unclamped state, in addition to a striker device (3). The aim of the invention is to simplify the safe and precise insertion thereof such that a guide rail (23) for a striker element is arranged in a fixed manner on the clamping device (2) and is oriented in such a manner that a path, which is determined by the guide rail, leads to an end face of the endoprosthesis (1) which is held in the clamping device (2).

17 Claims, 2 Drawing Sheets

U.S. PATENT DOCUMENTS

| | | | |
|---|---|---|---|
| 6,113,605 A * | 9/2000 | Storer | 606/99 |
| 6,165,177 A * | 12/2000 | Wilson et al. | 606/100 |
| 6,322,564 B1 | 11/2001 | Surma | |
| 2003/0233100 A1 * | 12/2003 | Santarella et al. | 606/99 |

FOREIGN PATENT DOCUMENTS

| | | |
|---|---|---|
| EP | 0 485 065 A | 5/1992 |
| EP | 852 931 | 7/1998 |
| EP | 956 824 | 11/1999 |
| FR | 2839641 A1 | 11/2003 |

\* cited by examiner

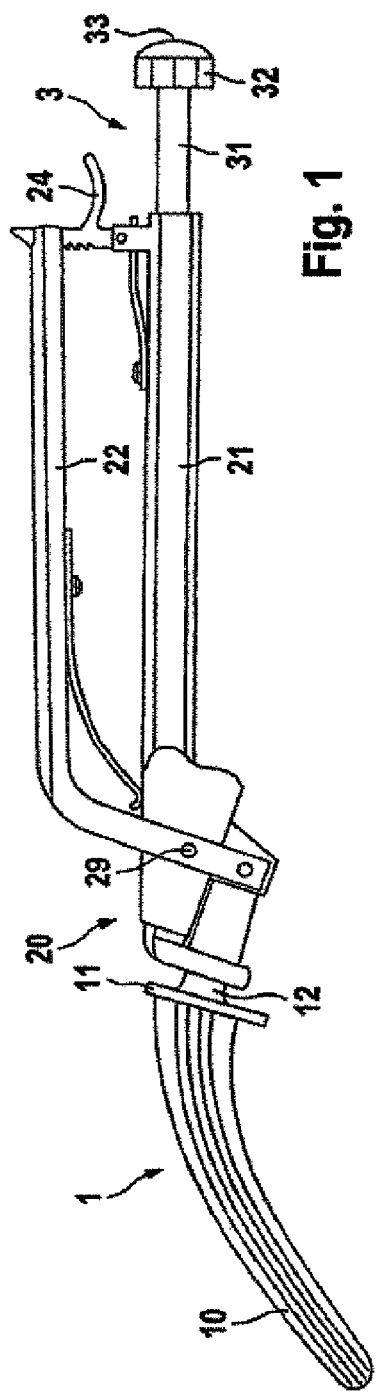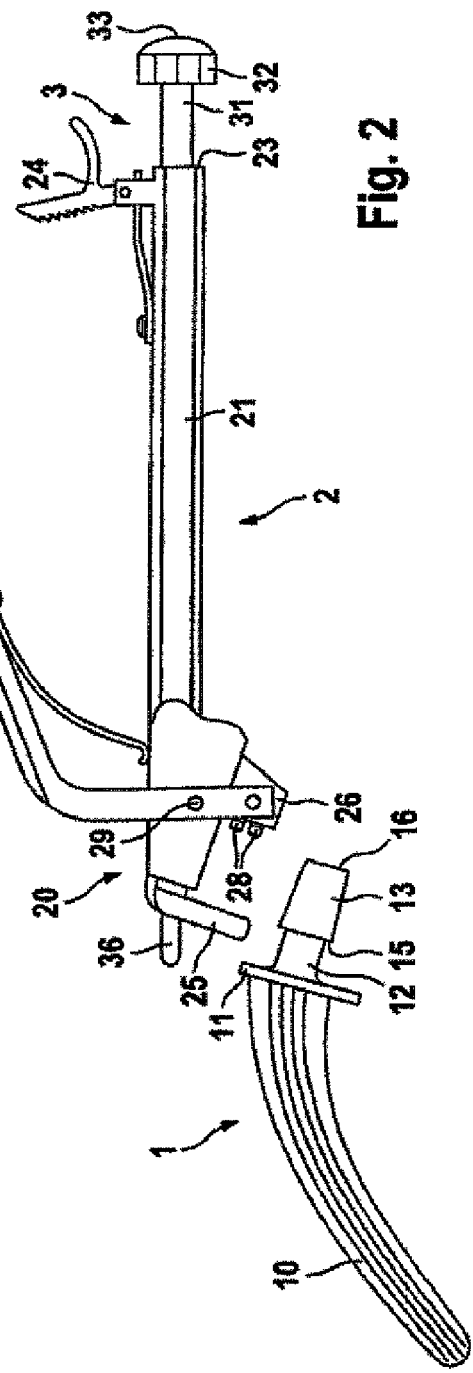

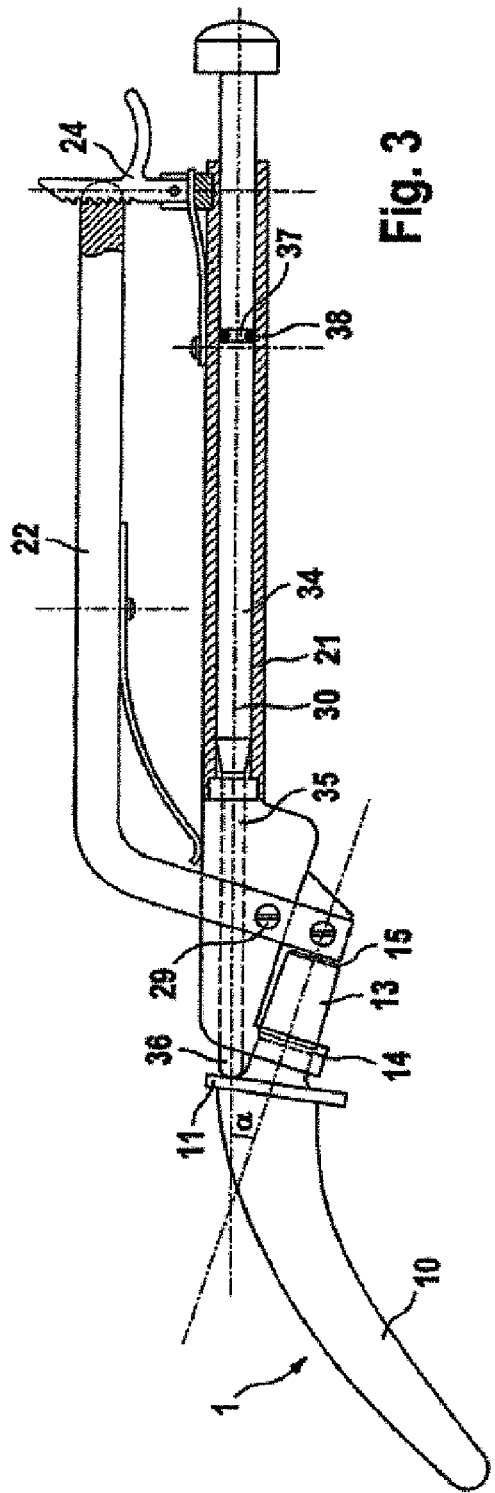
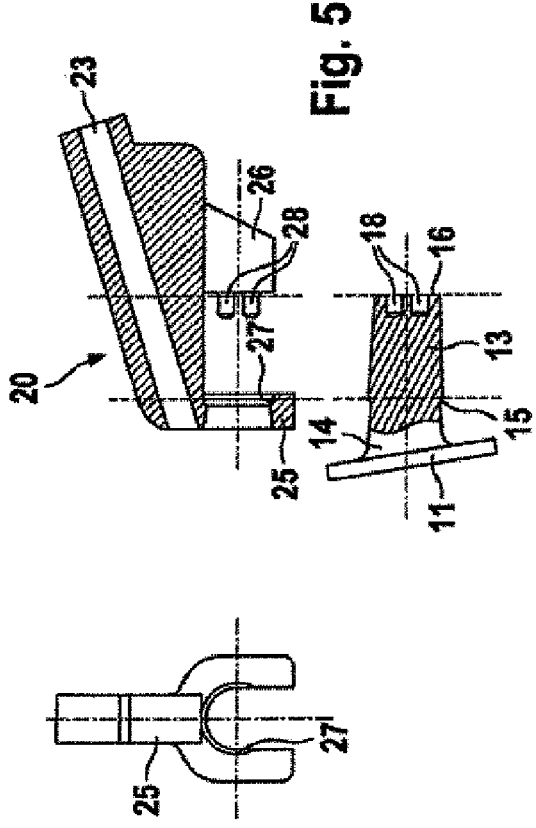

INSERTION INSTRUMENT FOR AN ENDOPROSTHESIS COMPRISING A PROSTHESIS SHAFT WHICH IS TO BE INSERTED INTO A MEDULLARY CAVITY

RELATED APPLICATION DATA

This patent is related to, claims priority benefit of and is a U.S. National Phase Application based on international application No. PCT/EP2006/08679, which was filed on Sep. 6, 2006, and which claim priority benefit of German national patent application No. 20 2005 014 270.0, which was filed on Sep. 9, 2005.

BACKGROUND

1. Field of the Invention

The invention concerns an insertion instrument for an endoprosthesis, comprising a neck part and a shaft part which is to be inserted into a medullary cavity, whereby the instrument comprises a clamping device with a holding fork and a thrust bearing, which are designed to maintain the prosthesis shaft in a clamped state and to release it in an unclamped state and also comprises a striker device.

2. Description of the Related Art

In order to join endoprostheses to the end of a tubular bone such as the femur, usually prosthesis shafts are provided which are introduced into a medullary cavity of the tubular bone. For this purpose, during the implantation of the prosthesis, the medullary cavity has to be opened, its inside removed to the required extent, and finally the shaft of the prosthesis is to be inserted. In order to achieve a solid and secure positioning of the prosthesis shaft in the tubular bone, the cavity to be created in the medullary cavity has to be adjusted to the contour of the shaft in order to be inserted as accurately as possible. Subsequent corrections of the position of the prosthesis shaft lead to widening of the cavity and thus to a less secure seat. The long-term stability of the prosthesis is thereby endangered. This applies especially when the implantation of the endoprosthesis is to be done without any cement.

Various instruments have become known with which the prosthesis can be implanted with its shaft. An insertion instrument is known from EP B 0 852 931, which has a grip part with a coupling onto which a rasp can be arranged for clearing the cavity in the medullary cavity or on which the shaft of the endoprosthesis to be inserted can be arranged. The rasp is designed as a profile rasp and serves to form a cavity corresponding to the contour of the shaft to be inserted. Once the cavity is created, the rasp can be removed from the grip end and the shaft of the endoprosthesis can be connected to the grip part. A similar insertion instrument is known from EP B 0 956 824. The grip part has a remote-controllable quick coupling, with the aid of which the rasp or the prosthesis shaft to be inserted is held on the grip part. Furthermore, on its back end away from the coupling, the grip part has an anvil. This serves as striking head. With this, when the shaft fits tightly in the medullary cavity, the endoprosthesis can be driven into its final position by hammer strokes.

A disadvantage of the insertion instruments of the state of the art lies in the fact that position changes, as they occur especially in the case of corrections, lead to a widening and thus to a worsening of the seat of the shaft in the medullary cavity of the bone. This applies especially when corrections are first made at the time of the hammering in. Moreover, it may occur inadvertently that due to difficult access conditions, the hammer strokes are done in an unfavorable direction onto the striking head. As a result of this, not only incorrect positioning of the shaft and thus of the prosthesis with respect to the bone occurs, but also the poorer seat would lead to the danger of premature loosening.

SUMMARY

The task of the invention is to improve an insertion instrument of the type mentioned at the outset so that a safer and more accurately positioned insertion is simplified.

The solution according to the invention lies in the characteristics of the independent claims. Advantageous further developments are the objects of the dependent claims.

According to the invention, in an insertion instrument for an endoprosthesis, that comprises a neck part and a shaft part which is to be inserted into the medullary cavity, comprising a clamping device with a holding fork and a thrust bearing, which are designed so that in a clamped state the endoprosthesis is held fixedly and in an unclamped state it is released, and a striker device, it is provided, that a guide rail for a striking element is arranged fixedly on the clamping device and is aligned so that a path determined by the guide rail leads to an end face of the endoprosthesis which is held in the clamping device.

First of all, a few concepts will be explained:

A holding fork is defined as a holder that is open on one side, so that the held object can be introduced into the holder or removed from it. The opening can be closed with a lock when the object is introduced, but this is not a requirement.

A thrust bearing is an element designed for the transfer of pressing forces, arranged opposite the holding fork such that the part of the endoprosthesis to be held is clamped between them.

A guide rail is an arrangement that provides a position as well as a movement direction (path) for the striker element.

The invention is based on the idea that accurately positioned insertion of the shaft part of the prosthesis into the medullary cavity is achieved with the insertion instrument in such a way that the position of the prosthesis is accurately defined both during introduction and striking in. Accurate guidance of the prosthesis is ensured with the insertion instrument according to the invention not only during the phase of introduction into the medullary cavity but also beyond that during the striking-in phase. With the guide arranged in the insertion instrument according to the invention, the striking force is successfully applied to the prosthesis to be inserted in an accurately defined manner. Incorrect positioning that may arise due to unavoidable variations of an unguided striking instrument, such as a hammer guided freely by hand, is effectively avoided. This is a great advantage especially when the accessibility of the implantation location to the operator is limited. Conventionally, deviations occur under difficult implantation circumstances, due to the fact that it is not possible to guide the striker device using the full extension of the holding instrument, which leads to erroneous positioning. With the insertion instrument designed according to the invention, even under such difficult conditions, implantation with accurate positioning can be achieved in a simple and safe manner.

Although not absolutely necessary, it is expedient for the guide rail to be closed on the side. This is especially preferred when it is designed as a tube. Then it may function at the same time as a part of the handle for gripping by the operator. The closed design prevents entry of foreign bodies. In this way the danger of blocking or jamming of the striking element in the guide rail is almost completely eliminated.

It is especially preferred for the striking element to be a ram inserted into the guide rail. Due to its elongated shape, the ram is guided optimally inside the guide rail which is designed preferably as a tube with an inner shape of the same contour. However, the shaft of the ram does not only serve for guiding, but rather, due to its not insignificant mass, because of its relatively long extension, it already serves as a striking element itself. Therefore, a striking head that is provided optionally at the end of the ram can be designed to be smaller. In this way, the insertion instrument can be designed with a relatively low additional weight and due to the distributed mass of the ram is balanced in a more favorable way for handling. The striking head is preferably designed as a handle. In this way the ram can be operated by hand too, and it can be used as a striking head as well, with its back side designed as an anvil surface.

The ram has a tip on its front end that is preferably rounded. The advantage, in comparison to a stub tip, is that when it hits the end face of the endoprosthesis at an angle, the danger of notching and damage is reduced. Notching or other damage would lead to a weakening of the prosthesis material at this location, which would lead to a corresponding reduction of the stability and thus to the long-term life of the prosthesis. The rounded design of the tip also has an advantage when the end face of the prosthesis receiving the strike of the ram is not completely plane.

As already mentioned, the insertion instrument is well balanced due to the mass distribution of the ram. In order to retain this favorable handling property even when the prosthesis is being driven in during use of the ram, the ram is expediently provided with a recoil damper. This serves to prevent or at least reduce a rebounding of the ram. Such a rebound would act as a recoil and lead to the danger of undesired change of position of the insertion instrument. This is counteracted by the recoil damper. The additional expenditure required for the recoil damper is extremely small. It may even be sufficient to provide a friction element on the shaft of the ram, which exercises a frictional force on the guide rail. It is especially advantageous to form a peripheral groove on the shaft of the ram into which an O-ring is inserted. The dimensions of the O-ring are chosen so that it abuts to the inside wall of the guide rail designed as a tube.

Advantageously, the ram has a segmented design, whereby one segment has a smaller cross-section than the other. When the segment with the smaller cross-section lies in the forward position, looking in the direction of the holding device, then with the shoulder that is formed at the transition to the segment with the wider cross-section, a depth stop for the ram can be formed. In this way, the danger of a sliding out and of an excessively wide driving of the ram toward the implanted endoprosthesis is minimized. The stepwise narrowing of the shaft to the tip thus formed permits not only the forming of a stop, but also facilitates the replacement of the O-ring from the tip of the ram.

According to a further aspect of the invention, a position marker is provided on the clamping device, for a correct angular position of the endoprosthesis to the insertion instrument. Thus, the operator has an indication available, that is simple to use, so that the prosthesis is held in the correct angular orientation to the insertion instrument. The position marker can be achieved in different ways, in the simplest way by markings. It was found to be useful to provide the position markings as projections on the clamping device designed for moving into engagement into a recess on the endoprosthesis in the clamped state. Having the protrusions lock only in the correct angular position in the particular recess on the endoprosthesis ensures that the endoprosthesis can be fixed in its relative position to the insertion instrument in a simple and expedient manner. Visual control of the orientation is superfluous. The orientation remains even under difficult circumstances in case of poor accessibility, or, if necessary, it can also be restored easily without any visual contact. Preferably, the projection is arranged on the thrust bearing and is dimensioned so that it is about 0.1 mm to 1 mm larger than the depth of the recess in an end face of the endoprosthesis. In this way it is achieved that the contact between the thrust bearing and the endoprosthesis is via the projections, or more accurately that the tips of the projections abut on the base of the recesses. The thrust bearing does not have to have any contact with the endoprosthesis otherwise; specifically, the thrust bearing can remain away from the end face of the endoprosthesis. This is an advantage not to be underestimated, since frequently the end face of the endoprosthesis is a part of an exactly-dimensioned holding part, which must be protected as much as possible against damage to ensure accurate positioning of the joint connecting components.

In an expedient embodiment the holding fork is designed so that a seat for an anchoring cone of the holding part is incorporated in it. The anchoring cone is taken up in the seat with its lower edge in the holding fork. Hereby the seat does not have to have a large depth, a depth of up to 2.5 mm, preferably 1 mm, usually is sufficient. It is achieved with this seat that the holding fork has to act on the anchoring cone only in the lower edge region. Thus, the sensitive cone surface remains protected from [adverse] effects by means of the holding fork. Damage of the surface can be prevented in this way.

BRIEF DESCRIPTION OF THE DRAWINGS

The invention will be described in more detail below with reference to the attached drawings, in which a practical example is shown. The following are shown:

FIG. 1 a top view of a practical example for an insertion instrument according to the invention in the clamped state with an endoprosthesis;

FIG. 2 a view of the insertion instrument according to FIG. 1 in the unclamped state;

FIG. 3 a partial section through the insertion instrument represented in FIG. 1;

FIG. 4 a front view of a part of a clamping device of the insertion instrument represented in FIG. 1; and FIG. 5 a partial cross-section of the clamping device with the endoprosthesis to be held.

DETAILED DESCRIPTION OF THE DISCLOSURE

The insertion instrument according to the practical example has the general basic shape of a pair of tongs with a grip part in the back region and a clamping part (referred to below as clamping device) 29 in the front region. The two regions are separated by a swivel joint 29. The grip part has 2 hand grips 21, 22 which extend toward the back, like rods. They can be secured in a pushed-together position with the aid of a locking device 24.

The clamping device 20 is arranged at the front end of the insertion instrument, which is designated with the reference number 2 in its entirety. The clamping device consists essentially of a fork 25 at the front end of the leg connected to the hand grip 21. The fork 25 has a receiving opening into which the endoprosthesis 1 to be clamped is to be inserted. The clamping device 20 has a thrust bearing further towards the front end of the leg formed by the hand grip 22. It is formed by a sliding block 26 which is arranged pivotable on the front end so that it performs a sliding forward and backward movement when the clamping device 20 is closed and opened. The sliding block 26 has an end face facing the holding fork 25, and two projections 28 are arranged on this. The projections are designed as pins and have a length of about 4 mm. They are oriented so that they are directed towards the holding fork 25, mainly to its opening region.

Now the structure of the guide rails in the insertion instrument is described. The hand grip 21 is designed in a tubular form in its back region. It has a bore 23, which extends along its entire length. It functions as guide rail for a ram 31. The ram 31 is designed as a striking tool and consists essentially of its shaft, divided into two segments 34, 35, with a rounded tip 36. A handle 32 is arranged at the back end of the ram 31 for use by the operator. The ram 31 like the rest of the insertion instrument is made of stainless steel. Due to the mass of the ram 31 including the handle 32, in many cases a sufficient striking effect can be achieved merely by hand strength. In case a stronger striking effect is required, the back side of the handle 32 is provided with an anvil surface 33. Hammer strokes can be applied to this, through which the striking action transferred to the tip 36 can be increased significantly.

On the outer surface of ram 31, in the region of the first segment 34, a peripheral groove 37 is formed. An O-ring 38 is arranged in this. It is dimensioned so that it does not close the surface of the shaft segment 34 in a flush manner, but it protrudes to such an extent that it contacts the inner wall of bore 31. In this way, the O-ring exercises a frictional force that works against the movement of ram 31. Thus, the O-ring 38 can largely prevent the recoil of the ram 31 after the striking action, especially in case of hammer strikes onto the anvil surface 33.

In order to explain the mode of action of the insertion instrument, now the endoprosthesis to be implanted will be presented briefly. The endoprosthesis is a shaft prosthesis, as it forms the femur component of a total hip joint prosthesis. The shaft prosthesis consists essentially of a long extended bent shaft part 10, a supporting collar 11 and a neck part 14 extending out from the supporting collar 11. A cone 13 is formed in the outer region of the neck part 14. It serves to hold the ball of a joint. The surface of the cone 13 as well as its end face 16 hereby define the positioning of the ball of the joint (not shown). They are manufactured precisely and must be protected against damage. The shaft part 10 serves for being implanted into the medullary cavity of the previously opened) femur. The shaft part 10 can designed for cemented or cement-free implantation. Especially in the case of cement-free implantation, a good form fit to the surrounding structure in the medullary cavity is important. Changes of direction of the endoprosthesis 1 or of the shaft part 10 during the insertion or the striking in lead to widening in the medullary cavity, through which the form fit will be influenced adversely, and thus the stability and security of the anchoring of the endoprosthesis in the femur bone is reduced. In order to make possible safe guidance of the endoprosthesis 1 during insertion and striking in, it is clamped fixedly to the insertion instrument 2. This is done with the clamping device 20 in the manner that is described below.

The clamping device 20, with its holding fork 25 and its thrust bearing 26 is designed to hold the endoprosthesis 1 on the cone 13 of the neck part 14. A circular step is incorporated into holding fork 25, which serves as seat 27 for the lower edge 15 of cone 13. The depth of the seat 27 is chosen so that the cone 13 is inserted to a depth of about 1 mm into the holding fork 25. Only in this region, does contact occur between the holding fork 25 and cone 13. This area is typically non-critical for joining to the ball of the joint since the balls of the joints do not extend as far onto the cone 13. The seat 27 does not engage in the remaining area of the cone 13, so this is protected against damage. The thrust bearing 26 cooperates with the end face 16 of cone 13. However, it doesn't abut directly against the end face 16, but rather engages with its protrusions 28 into the corresponding recesses 18 on the end face 16 of cone 13. Hereby, the height of the projections 28 is somewhat greater than the depth of the recesses 18. A height of 4 mm for the projections 28 and a depth of 3 mm for the recesses 18 were proven to be suitable. In this way it is achieved that the projections 28 rest with their tip in the bottom of recesses 18 without the end face 16 itself being touched by sliding block 26. A safety gap of about 1 mm remains. The sliding block 26 with the projections 28 is moved forward by pressing together the grip parts 21 and 22 (in the clamping direction). Thereupon the projections 28 are inserted into recesses 18 and press the cone 13 with its lower edge 15 into the seat 27 of holding fork 25. The endoprosthesis 1 is thereby clamped fixedly onto the insertion instrument. The angular position is defined by the projections 28. Thus, they also function as position markers. The prosthesis 1 can be guided now by the operator safely and accurately with regard to position.

In the first step of the implantation, the prosthesis 1 with its shaft 10 is introduced into the medullary cavity with the aid of insertion instrument 2. Mostly this is successfully achieved to about ⅔ to ¾ of the length of the shaft 10 because of its conicity without application of any special force. After that, the increasingly tighter seat of the prosthesis shaft 10 in the bed of the medullary cavity requires an increasingly larger force, until the endoprosthesis 1 must be struck into the final position. This can occur with the insertion instrument according to the invention without having to put down the instrument. The operator works the ram 31 by means of the handle 32. The arrangement of the holding fork 25 with the thrust bearing 26 is hereby adjusted to the position of the bore 23 in such a way that the guide path 30 of the ram determined by it is chosen so that the tip 36 impinges on the endoprosthesis 1 at the collar 11. Thus the pulse transferred by the ram 31 is applied directly to the collar 11 and thus guided onto the shaft 10 without applying a load to the cone 13 and neck part 14. This direct transfer is not merely protective of the cone 13 and the neck part 14 of the endoprosthesis 1, but it also makes it possible to achieve a high driving action with relatively weak impact by the ram 31.

The angle of the arrangement of the endoprosthesis relative to the path 30 of the ram (angle α) is about 20 degrees to 40 degrees (preferably 25 degrees) and is chosen so that in the position of the endoprosthesis 1 in which the highest force is needed for striking in, the guide path 30 lies approximately perpendicular to the dissection surface at the bone. In this way, for this section that requires the application of an especially strong force, optimum force transfer is ensured.

In the insertion instrument according to the invention, the endoprosthesis can be clamped accurately with regard to position and angle onto the insertion instrument and then can be inserted precisely into the medullary cavity in this well defined position. The additional striking required for reaching the fixed end position of the prosthesis can be carried out with the insertion instrument, whereby by means of the guiding of the ram 31 it is ensured that the impulse forces are transferred by the striking to a favorable position on the collar 11 of the endoprosthesis 1. The sensitive cone 13 of the endoprosthesis 1 is hereby protected against the application of striking forces. The striking in can be carried out using the integrated ram 31 without changing the instrument. If necessary, additional force can be applied with a hammer via the anvil surface 33 at the back end of the ram 31.

The invention claimed is:

1. A combination surgical instrument and endoprosthesis comprising:
   an endoprosthesis having a neck part with a cone, a shaft part to be inserted into a medullary cavity, an end face on the cone, and recesses on the end face of the cone;
   an instrument having a clamping device with a holding fork and a thrust bearing, a striker device, a striking element, and a guide rail for the striking element; and
   position markers for rotationally positioning the endoprosthesis, the position markers including projections on the thrust bearing positioned to engage the recesses on the end face of the cone when clamped by the clamping device for inserting the endoprosthesis.

2. A combination according to claim 1, wherein the holding fork and clamping device are configured to hold the endoprosthesis fixedly in a clamped state and to release it in an unclamped state.

3. A combination according to claim 1, wherein the cone is taken up in a seat of the holding fork when clamped by the clamping device.

4. A combination according to claim 1, wherein the thrust bearing cooperates with the end face of the cone when the cone is clamped between the thrust bearing and the seat of the holding fork.

5. An insertion instrument and endoprosthesis combination comprising:
   the endoprosthesis having
      a shaft part to be inserted into a medullary cavity,
      a collar,
      a striking face at the collar,
      a neck part having a cone with an end face, and
      recesses on the end face of the cone; and
   the instrument having
      a clamping device with a holding fork and a thrust bearing, which are designed to hold the endoprosthesis fixedly in a clamped state and to release it in an unclamped state,
      a striker device, and
      a guide rail for a striking element arranged in a fixed manner on the clamping device and oriented so that a path determined by the guide rail leads to the striking face at the collar when the endoprosthesis is clamped in the clamping device,
   wherein the cone is taken up in a seat of the holding fork,
   wherein the thrust bearing cooperates with the end face of the cone for clamping the cone between the thrust bearing and the seat of the holding fork, and
   wherein position markers for a correct angular positioning of the endoprosthesis are provided on the thrust bearing as projections that engage in the recesses on the end face of the cone in the clamped state.

6. An insertion instrument according to claim 5, wherein the guide rail is closed.

7. An insertion instrument according to claim 6, wherein the guide rail is a tube.

8. An insertion instrument according to claim 5, wherein the seat has a depth of less than 2 mm.

9. An insertion instrument according to claim 5, wherein the striking element is a ram inserted into the guide rail.

10. An insertion instrument according to claim 9, wherein the ram has a handle on its back end away from the endoprosthesis.

11. An insertion instrument according to claim 10, wherein the handle has a striking surface.

12. An insertion instrument according to claim 9, wherein the ram has a rounded tip.

13. An insertion instrument according to claim 9, wherein a recoil damper is provided for the ram.

14. An insertion instrument according to claim 13, wherein the recoil damper is designed as an O-ring arranged in a peripheral groove.

15. An insertion instrument according to claim 9, wherein the ram is segmented, whereby one segment has a smaller cross-section than the other segment.

16. An insertion instrument according to claim 5, wherein the projections are about 0.1 mm to about 1 mm longer than the depths of the recesses.

17. An insertion instrument according to claim 5, wherein the seat has a depth of less than 1 mm.

* * * * *